(12) United States Patent
Larson et al.

(10) Patent No.: US 8,486,691 B2
(45) Date of Patent: Jul. 16, 2013

(54) APPARATUS FOR ASSESSING THE EFFECTIVENESS OF A STERILIZATION PROCESS

(75) Inventors: Kent Larson, Woodbury, MN (US);
Patrick LaValley, Elk River, MN (US);
Jami McLaren, Crystal, MN (US);
Steven J. Olson, Mahtomedi, MN (US)

(73) Assignee: Sterilucent, Inc., Minneapolis, MN (US)

( * ) Notice: Subject to any disclaimer, the term of this patent is extended or adjusted under 35 U.S.C. 154(b) by 493 days.

(21) Appl. No.: 12/758,288

(22) Filed: Apr. 12, 2010

(65) Prior Publication Data

US 2011/0250677 A1    Oct. 13, 2011

(51) Int. Cl.
*C12Q 1/22* (2006.01)
*G01N 31/00* (2006.01)
*G01N 31/22* (2006.01)
*C12M 1/12* (2006.01)
*A61L 2/00* (2006.01)

(52) U.S. Cl.
USPC ............. 435/287.4; 435/31; 422/416; 422/29

(58) Field of Classification Search
USPC ............................ 435/287.4, 31; 422/416, 29
See application file for complete search history.

(56) References Cited

U.S. PATENT DOCUMENTS

| | | | |
|---|---|---|---|
| 3,930,690 A * | 1/1976 | Broyhill | 384/130 |
| 4,839,291 A | 6/1989 | Welsh et al. | |
| 5,552,320 A | 9/1996 | Smith | |
| 5,830,683 A | 11/1998 | Hendricks et al. | |
| 5,866,356 A * | 2/1999 | Albert et al. | 435/31 |
| 5,872,004 A * | 2/1999 | Bolsen | 435/287.4 |
| 5,876,331 A * | 3/1999 | Wu et al. | 600/139 |
| 5,942,408 A | 8/1999 | Christensen et al. | |
| 6,355,448 B1 * | 3/2002 | Foltz et al. | 435/31 |
| 6,551,555 B2 | 4/2003 | Antonoplos et al. | |
| 6,653,096 B1 | 11/2003 | Christensen et al. | |
| 6,773,898 B1 | 8/2004 | Nyberg et al. | |
| 6,815,206 B2 | 11/2004 | Lin et al. | |
| 6,897,059 B2 * | 5/2005 | Foltz et al. | 435/287.6 |
| 7,045,343 B2 * | 5/2006 | Witcher et al. | 435/287.6 |
| 7,091,042 B2 | 8/2006 | Lemus et al. | |
| 7,247,482 B2 | 7/2007 | Lemus et al. | |
| 2004/0248235 A1 * | 12/2004 | Foltz et al. | 435/31 |
| 2007/0178549 A1 | 8/2007 | Kaiser | |
| 2008/0261296 A1 * | 10/2008 | Justi et al. | 435/287.4 |
| 2008/0317626 A1 * | 12/2008 | Arnold et al. | 422/29 |

* cited by examiner

*Primary Examiner* — Nathan Bowers
*Assistant Examiner* — Gautam Prakash
(74) *Attorney, Agent, or Firm* — Nikolai & Mersereau, P.A.; Thomas J. Nikolai

(57) ABSTRACT

A device useful in determining the efficacy of a chemical sterilization process includes a dead end cavity closed by an access cap having a port coupled to a challenge tube defining the only path by which a substantial quantity of sterilant can reach the cavity. A biological indicator is located within the cavity and a chemical indicator is also provided. These indicators, and particularly the biological indicator, provide an indication of whether chemical sterilant would reach all interior exposed surfaces of a load in sufficient concentrations to adequately sterilize the load.

26 Claims, 2 Drawing Sheets

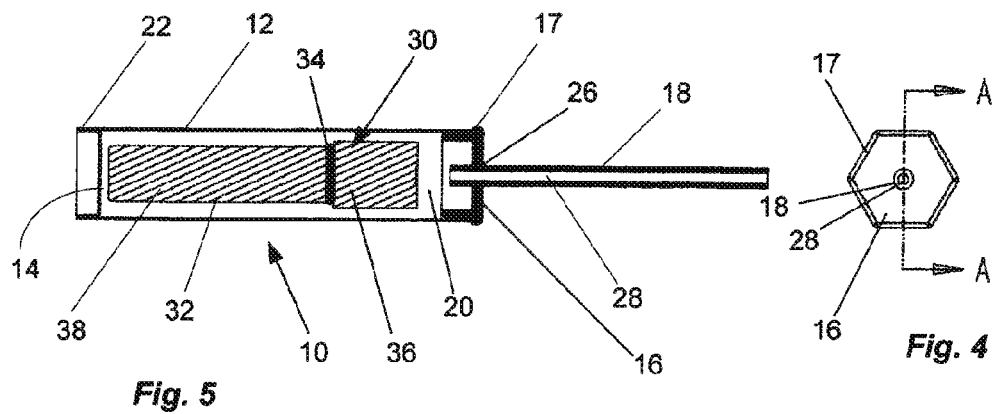
Fig. 5
Fig. 4
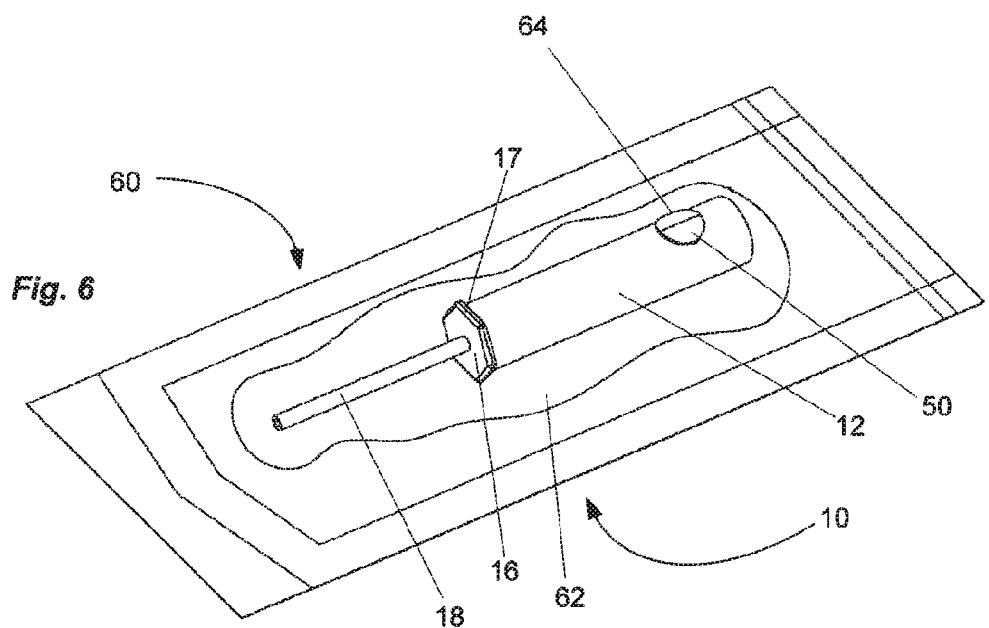
Fig. 6

APPARATUS FOR ASSESSING THE EFFECTIVENESS OF A STERILIZATION PROCESS

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Contract No. W81XWH-05-1-0398 awarded by USA Medical Research ACQ Activity; Office of Naval Research SBIR Phase II, Contract No. N00014-06-M-0301 and Contract No. 5R44HL074653-03 awarded by National Institute of Health SBIR Phase II.

CROSS-REFERENCED TO RELATED APPLICATIONS

Not applicable.

BACKGROUND OF THE INVENTION

I. Field of the Invention

The present invention relates to evaluating the efficacy of sterilization processes. More specifically, the present invention provides a useful tool for evaluating whether a sterilization process effectively deactivates biological contaminants within a load to be sterilized, including contaminants residing within the most difficult-to-sterilize locations of the load.

II. Related Art

Various sterilization processes have been employed to eliminate biological contaminants from a load. Such a load, for example, may comprise one or more medical or dental instruments or supplies. Some of these sterilization processes involve the use of a sterilant chemical chosen because it will destroy bacteria and other biological contaminants on the surface of a load if delivered to the surface at an appropriate concentration and for an appropriate period of time. One commonly used sterilant chemical is hydrogen peroxide. When the load has interior exposed surfaces, sterilization will only be successful if the entirety of all interior exposed surfaces is brought into contact with the sterilant at sufficient concentrations and for a sufficient period of time to destroy all biological contaminants present on such surfaces. Biological contaminants not eradicated from medical or dental instruments or supplies prior to use can be transferred to a patient leading to infection.

Much research has been undertaken to develop effective chemical-based sterilization processes. Various test packs have also been developed to attempt to test the efficacy of such processes. These test packs typically provide various paths from the exterior of the test pack to an interior chamber where one or more indicators are located. These indicators often include a chemical indicator which changes color when exposed to the sterilant. These indicators also often include a biological indicator housing organisms which are deactivated if sterilant of a sufficient concentration reaches the biological indicator over a sufficient period of time. Such devices are sometimes referred to as "process challenge devices" because they are intended to present a defined challenge for test purposes comparable to the challenge presented by the most difficult item to be sterilized in a load to be sterilized.

Existing process challenge devices suffer from a variety of problems leading to inaccurate test results. Some problems result from blockage of the aforementioned paths. Such blockage can occur as a result of condensation occluding the path between the interior and exterior of the device. Such blockages can also be the result of pressure changes in the sterilization chamber related to the process being tested causing the walls surrounding the path to collapse. Other problems arise if the challenge presented is either more or less difficult than required given the attributes of the contents of a load to be sterilized. Still other problems arise as a result of the number and spacing of access points into the path from the exterior of the test pack. When multiple access points are present, controlling the degree of challenge is made more difficult and obtaining repeatable test results becomes problematic. Existing process challenge devices are also often difficult or expensive to manufacture. The present invention overcomes these and other problems.

SUMMARY OF THE INVENTION

The present invention relates to process challenge devices used to test the efficacy of sterilization equipment, methods and protocols. In one embodiment, the process challenge device comprises an assembly including a housing having a first dead end, a second open end, and an interior cavity. The dead end can be formed using a plug or by forming the housing to provide the dead end. The assembly further comprises an access cap sealing the open end of the housing. The access cap has a port. Coupled to the port is a challenge tube having a lumen extending along the entire length of the challenge tube. The challenge tube is joined to the port of the access cap such that the only path by which a substantial quantity of sterilant can enter the cavity is the path defined by the lumen of the challenge tube and the port. The length of the challenge tube and diameter of the lumen are selected to present a desired challenge.

Before sealing the open end of the housing with the access cap, a biological indicator is positioned within the cavity. In some embodiments, the assembly may also include a sterilization pouch surrounding the housing and challenge tube. Whether or not such a pouch is used, a chemical indicator is coupled to the assembly. The chemical indicator can be placed within the interior cavity of the housing or otherwise affixed to the housing, plug, access cap, challenge tube, or sterilization pouch of the assembly. The chemical indicator provides an immediate visual indication (such as a color change) when a predetermined amount of sterilant has come into contact with the chemical indicator.

The biological indicator may, but need not be, self-contained. Self-contained biological indicators typically include a known load of microorganisms and a medium, that when brought into contact with any viable microorganisms, will provide an indication of the presence of viable microorganisms. Other biological indicators only include a load of microorganisms. After the test, the load of microorganisms is then tested to see if any remain viable.

Process challenge devices made in accordance with the present invention are used to periodically verify, through chemical and biological evaluation, that a sterilizer and the sterilization process carried out using the sterilizer are fully functional. For example, process challenge devices are used both for installation qualification of a sterilizer and routine verification of sterilizer operation. The process challenge device provides a challenge between the sterilizing environment and the biological and chemical indicators intended to represent the most challenging location for sterilant to reach in an actual load to be sterilized. Sterilant must overcome the challenge posed by the process challenge device to trigger a passing response from the biological indicator and chemical indicator if a chemical indicator is provided, thus indicating the sterilization process carried out using the sterilizer is effective.

BRIEF DESCRIPTION OF THE DRAWINGS

FIG. 4 is an end view of the process challenge device shown in FIG. 1.

FIG. 5 is a sectional view of the process challenge device taken along the line A-A in FIG. 4.

FIG. 6 is a perspective view of a second embodiment of the process challenge device of the present invention.

DETAILED DESCRIPTION OF THE INVENTION

Figure 1:
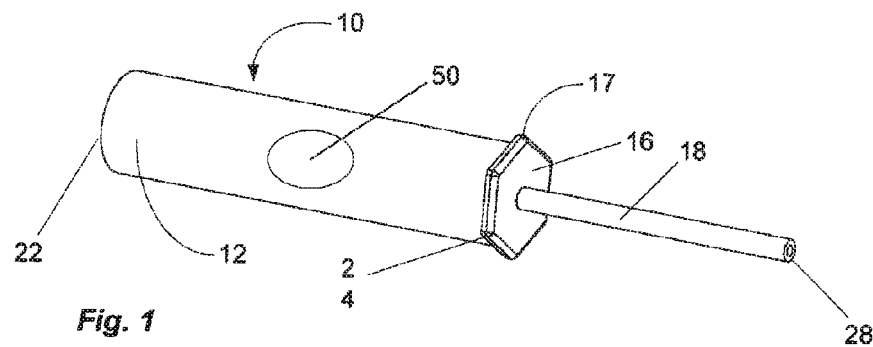
FIG. 1 is a perspective view of a first embodiment of the process challenge device of the present invention.
Figure 2:
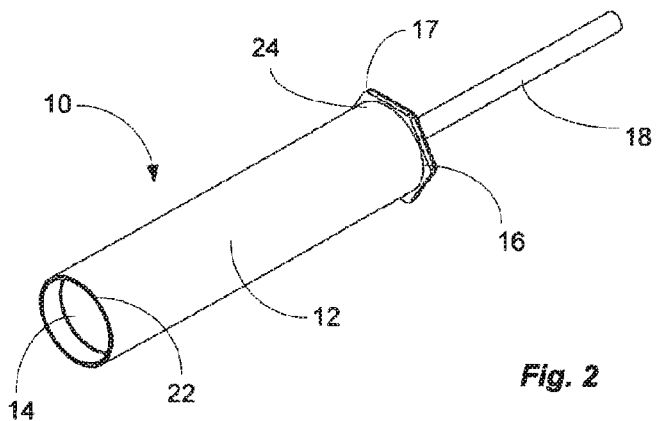
FIG. 2 is another perspective view of the process challenge device shown in FIG. 1.

The process challenge device of the present invention provides an inexpensive, easy-to-assemble and disposable device used to verify that a sterilizer and associated sterilization process are fully functional to destroy biological containments in a load. As shown in FIGS. 1-5, the process challenge device 10 comprises a housing 12, a plug 14, an access cap 16 and a challenge tube 18. As shown in FIG. 6, the process challenge device 10 may also include a sterilization pouch 60. The process challenge device 10 also includes a biological indicator 30 and an optional chemical indictor 50.

The plug 14 closes one end of the tubular-shaped housing 12 to provide the housing 12 with a cavity 20 with a dead end 22. Those skilled in the art will recognize that the housing 12 can be formed in a way in which the dead end 22 of cavity 20 is created without a plug 14.

Figure 3:
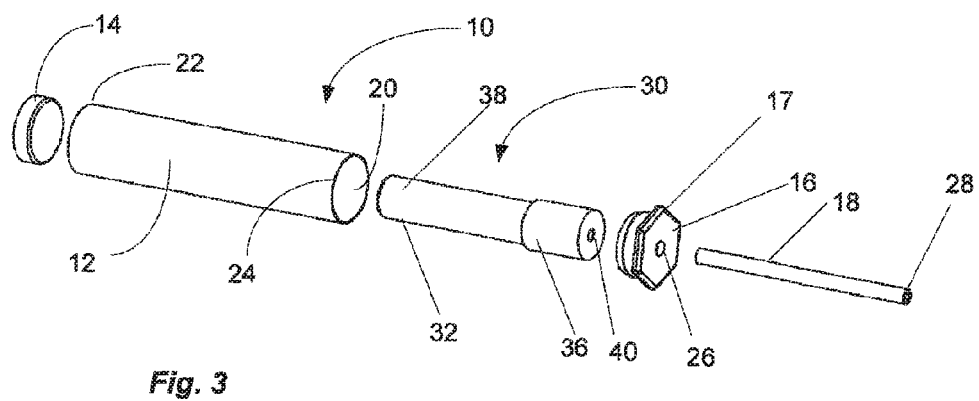
FIG. 3 is an exploded view of the process challenge device shown in FIG. 1.

The other end 24, referred to as the open end, of the housing 12 is closed by access cap 16. The access cap has a flange 17 to facilitate removal of the access cap 16 from the housing 12. The access cap 16 has a port 26 extending through the access cap 16 to which the challenge tube 18 is coupled as best shown in FIGS. 3 and 5. Tube 18 has a lumen 28 extending its entire length. When the process challenge device 10 is fully assembled, the only path by which a substantial quantity of sterilant can enter the dead end cavity 20 is the path defined by lumen 28. The length and diameter of the lumen 28 of the challenge tube 18 are selected to present the desired challenge and, more specifically, a challenge commensurate with the most challenging location for sterilant to reach in an actual load to be sterilized.

As best shown in FIGS. 3 and 5, a biological indicator 30 is positioned within the dead end cavity 20. The biological indicator 30 shown is self-contained within its own housing 32 which is divided by a wall 34 into two sections 36 and 38. Section 36 contains a known load of viable microorganisms. Section 38 contains a medium, that when brought into contact with viable microorganisms, will provide an indication of the presence of viable microorganisms. As best shown in FIG. 3, the housing 32 of the biological indicator 30 has a port 40 through which sterilant can pass into section 36. The microorganisms within section 36 will all be deactivated if an adequate quantity of sterilant enters section 36. This can be determined by rupturing the wall 34, comingling the medium with the microorganisms, and checking the medium to see if it indicates the presence of any viable microorganisms. The biological indicator 30, as shown, is only one of many different types of biological indicators which may be used without deviating from the invention. Some suitable biological indicators are self-contained as is indicator 30, while other suitable biological indicators are not. Depending on the biological indicator employed, the user may incubate the biological indicator after it is subjected to the sterilization process to promote the growth and reproduction of microorganisms surviving the sterilization process being evaluated.

Suitable biological indicators 50 are manufactured by various companies. One such biological indicator has a housing containing a disk coated with microorganisms and an ampoule containing a medium which will change color if the ampoule is broken and the medium comes into contact with viable microorganisms. The housing has a filtered opening through which sterilant can enter to deactivate the microorganisms.

FIG. 1 also shows a chemical indicator 50 adhered to the outer wall of housing 12. The chemical indicator may also be coupled to the plug 14, the access cap 16 or the challenge tube 18. It may also be positioned within the dead end cavity 20 of the housing 12. The chemical indicator 50 is selected to react with the sterilant and provide an indication that sterilant has reached the indicator 50 in sufficient quantities to cause such a reaction (e.g., a color change). Thus, the chemical indicator 50 lets a user know whether the process challenge device 10 has been exposed to sterilant or not or, stated otherwise, whether the process challenge device 10 can still be used to, provide a reliable test. The chemical indicator 50 also provides a preliminary indication of the efficacy of the sterilization cycle. If the chemical indicator 50 has not reacted as a result of being subjected to the cycle, the user will know the cycle was ineffective without having to check the biological indicator 30.

The materials used to form the challenge tube 18 and the housing 12 will depend on the sterilant used in the sterilization equipment and protocol being tested. By way of example, when the sterilant is vaporous hydrogen peroxide, the challenge tube 18 and housing 12 are preferably made of materials which are compatible with the hydrogen peroxide. Such materials may include, but are not limited to, low density polyethylene, linear low density polyethylene high density polyethylene, polypropylene, polyethylene terepthalate glycol, polyethylene terepthalate, polyvinyl chloride fluoropolymers, thermoplastics, silicone, stainless steel, aluminum, and glass.

As shown by FIG. 3, the process challenge device is created by forming an assembly comprising: (1) the housing 12 having a dead end 22, an open end 24 and an interior cavity 20; (2) the biological indicator 30 within the cavity 20; (3) the access cap 16 which seals the open end 24 of the housing 12 and has a port 26; and (4) a challenge tube 18 having an interior lumen 28 extending the length of the challenge tube 18, coupled to the port 26 such that the only path by which a substantial quantity of sterilant can enter the cavity 20 is through the path defined by the lumen 28 and the port 26. The length of that challenge tube 18 and the diameter of the lumen 28 is selected to create a desired challenge.

FIG. 3 also shows that the dead end of cavity 20 can be provided by a plug 14. Sealants, heat, adhesives, gaskets, O-rings, an interference fit, a press fit, or other manufacturing methods can be used to create an acceptable interface between the housing 12 and the plug 14. These techniques can also be used to form an interface between the cavity 20 and the access cap 16 and the tube 18 and the access cap 16. As noted above, the plug 14 can be eliminated if the shape of the housing is otherwise fabricated or altered to provide the cavity 20 with a dead end. The tube 18 and access cap 16 can be integrally molded. Likewise, the entire assembly may be integrally molded.

As noted above, FIG. 6 shows the assembly may include sterilization pouch 60. Sterilization pouch 60 should be constructed of a material which is sufficient to contain the other components and assist in providing the desired challenge. An example of such a material is TYVEK®, a flash spun high density polyethylene fiber.

As shown in FIG. 6, the sterilization pouch 60 may include a transparent window 62 or may otherwise be made of a transparent material. Likewise, the housing 12 may include a transparent window 64 such that a user can look through the pouch 60 and transparent window 64 into the cavity 20. This is important if the chemical indicator 50 is positioned within the cavity 20 rather than, for example, attached to the exterior of the housing 12 as shown in FIG. 1. Of course, the window 64 can be eliminated if the chemical indicator 50 is positioned as shown in FIG. 1, is attached to the exterior of the plug 14, the access cap 16 or the challenge tube 18, or is simply placed inside pouch 60. Likewise, the pouch 60 need not be made of a transparent material or have a transparent window 62 if the chemical indicator 50 is coupled to the exterior of pouch 60. If the chemical indicator 50 is positioned outside of the housing 12, the housing 12 need not be made of a transparent material or include a transparent window 64.

When the embodiment shown in FIG. 6 is employed, the pouch 60 and its contents are placed in a sterilization chamber and subjected to a sterilization process to be tested. The chemical indicator is then checked to determine whether sterilant in sufficient quantities to trigger a response reached the chemical indicator 50. The assembly comprising housing 12, access cap 16, and tube 18 is removed from the pouch 60 and opened by gripping the housing 12 and the flange 17 of access cap 16 to disconnect the access cap 16 from the housing 12. The biological indicator 30 is removed from the dead end cavity 20. The biological indicator may then be processed as necessary to determine whether the microorganisms of the biological indicator were deactivated by the sterilization process.

The structural and operational features described above provide important advantages. The invention provides a single conduit through which sterilant passes to reach the biological indicator, thus providing an increased challenge for the sterilant to overcome. Substantial quantities of sterilant can only enter the dead end cavity 20 through the tube 18. The fact that cavity 20 is a dead-end cavity also provides an increased challenge while minimizing the space occupied by the invention. The invention provides flexibility in that it will accommodate the use of a variety of biological indicators, chemical indicators, and sterilants. The invention also provides a challenge device which is inexpensive, easy to manufacture and disposable.

Those skilled in the art will appreciate various changes may be made to the embodiments shown and described without deviating from the invention. For example, while the challenge tube 18 is shown as being straight, a curved challenge tube may also be used. The lumen is also shown as having a uniform diameter. The diameter of the lumen can be varied along its length. The pouch 60 need not be used. Other arrangements for coupling the challenge tube 18 to the cavity 20 may be employed. Thus, the invention to be covered is not intended to be limited by the foregoing description, but rather is defined by the following claims.

What is claimed is:

1. An apparatus for assessing the effectiveness of a sterilization process comprising:

a. an assembly comprising (i) a cylindrical housing having a first open end, a second open end, and an interior cavity; (ii) a plug sealing the first open end of the housing such that the cavity has a dead end; (iii) an access cap sealing the second open end of the housing, the access cap having a port; and (iv) a challenge tube, having a central lumen extending the length of the challenge tube, said challenge tube being coupled to the port so that the lumen provides the only path by which a substantial quantity of sterilant can enter the dead ended cavity; and
    b. a self-contained biological indicator positioned within the dead ended cavity.

2. The apparatus of claim 1 wherein the assembly further comprises a chemical indicator.

3. The apparatus of claim 1 wherein the length and diameter of the lumen of the challenge tube used are selected to present the desired challenge.

4. The apparatus claim 1 wherein the challenge tube and the housing are made of materials resistant to degradation by hydrogen peroxide.

5. The apparatus of claim 4 wherein the challenge tube and housing are constructed of materials selected from a group consisting of low density polyethylene, linear low density polyethylene, high density polyethylene, polypropylene, polyethylene terepthalate glycol, polyethylene terepthalate, polyvinyl chloride, fluoropolymers, thermoplastics, silicone, stainless steel, aluminum, and glass.

6. The apparatus of claim 1 wherein the access cap has a hex flange.

7. The apparatus of claim 1 wherein the housing comprises a transparent window area for viewing of the contents of the housing.

8. The apparatus of claim 1 wherein the assembly further comprises a sterilization pouch.

9. The apparatus of claim 1 wherein the self-contained biological indicator contains a known load of microorganisms and a medium that, when brought into contact with a load of viable microorganisms, will provide an indication of the presence of viable microorganisms.

10. The apparatus of claim 2 wherein the chemical indicator provides an immediate visual indication when a predetermined amount of sterilant has contacted the chemical indicator.

11. An apparatus for assessing the effectiveness of a sterilization process comprising:

a. an assembly comprising (i) a cylindrical housing having a first dead end, a second open end, and an interior cavity; (ii) an access cap sealing the second open end of the housing, the access cap having a port; and (iii) a challenge tube, having a central lumen extending the length of the challenge tube, the challenge tube being coupled to the port such that the only path by which a substantial quantity of fluid sterilant can enter the cavity is through the path defined by the lumen; and
    b. a self-contained biological indicator positioned within the cavity.

12. The apparatus of claim 11 further comprising a chemical indicator.

13. The apparatus of claim 11 wherein the length and diameter of the lumen of the challenge tube used is selected to accomplish the desired challenge.

14. The apparatus of claim 11 wherein the challenge tube and the housing are made of materials resistant to degradation by hydrogen peroxide.

15. The apparatus of claim 14 wherein the challenge tube and housing are constructed of materials selected from a group consisting of low density polyethylene, linear low density polyethylene, high density polyethylene, polypropylene, polyethylene terepthalate glycol, polyethylene terepthalate, polyvinyl chloride, fluoropolymers, thermoplastics, silicone, stainless steel, aluminum, and glass.

16. The apparatus of claim 11 wherein the access cap has a hex flange.

17. The apparatus of claim 11 wherein the housing comprises a transparent window area for viewing the contents of the housing.

18. The apparatus of claim 11 wherein the assembly further comprises a sterilization pouch.

19. The apparatus of claim 11 wherein the self-contained biological indicator contains a known load of microorganisms, and a medium that, when brought into contact with any viable microorganisms, will provide an indication of the presence of viable microorganisms.

20. The apparatus of claim 12 wherein the chemical indicator provides an immediate visual indication when a predetermined amount of sterilant has contacted the chemical indicator.

21. The apparatus of claim 20 wherein the chemical indicator is located on an exterior surface of the housing.

22. The apparatus of claim 20 wherein the chemical indicator is located within the housing.

23. A method for assembling an apparatus for assessing the effectiveness of a sterilization process comprising:
  a. forming an assembly comprising (i) a cylindrical housing having a first dead end, a second end, and an interior cavity; (ii) an access cap sealing the second open end of the housing, the access cap having a port, (iii) a challenge tube, having a central lumen extending the length of the challenge tube, the challenge tube being coupling to the port such that the only path by which a substantial quantity of fluid sterilant can enter the cavity is through the path defined by the lumen, the length of the challenge tube and the diameter of the lumen being selected to create a desired challenge; and (iv) a self-contained biological indicator positioned within the cavity;
  b. providing a chemical indicator; and
  c. packaging the assembly together with the chemical indicator in a sterilization pouch.

24. The method of claim 23 wherein the dead end of the housing comprises a plug.

25. The method of claim 23 wherein the access cap and challenge tube are integrally molded.

26. The method of claim 23 wherein the housing, access cap and challenge tube are integrally molded.

* * * * *